(12) United States Patent
Loudin et al.

(10) Patent No.: US 11,156,592 B2
(45) Date of Patent: Oct. 26, 2021

(54) UPFLOW COOLING STAGE FOR PHOTOLUMINESCENCE ANALYSIS

(71) Applicant: GEMOLOGICAL INSTITUTE OF AMERICA, INC. (GIA), Carlsbad, CA (US)

(72) Inventors: Lorne Loudin, Carlsbad, CA (US); Mehdi Toosi, Carlsbad, CA (US); Wuyi Wang, Edison, NJ (US)

(73) Assignee: Gemological Institute of America, Inc. (GIA), Carlsbad, CA (US)

( * ) Notice: Subject to any disclaimer, the term of this patent is extended or adjusted under 35 U.S.C. 154(b) by 69 days.

(21) Appl. No.: 16/005,311

(22) Filed: Jun. 11, 2018

(65) Prior Publication Data

US 2019/0376946 A1 Dec. 12, 2019

(51) Int. Cl.
*G01N 33/38* (2006.01)
*F25D 3/10* (2006.01)
*G01N 21/87* (2006.01)
*G01N 25/18* (2006.01)

(52) U.S. Cl.
CPC ............. *G01N 33/381* (2013.01); *F25D 3/10* (2013.01); *G01N 21/87* (2013.01); *G01N 25/18* (2013.01); *B01L 2300/1894* (2013.01)

(58) Field of Classification Search
CPC ...... G01N 25/18; G01N 21/01; G01N 33/381; G01N 21/87; B01L 2300/1894; F25D 3/10
See application file for complete search history.

(56) References Cited

U.S. PATENT DOCUMENTS

| 6,000,467 A | * | 12/1999 | Tokizaki | ................. | F28F 19/00 165/134.1 |
| 6,119,465 A | * | 9/2000 | Mullens | .................... | A01N 1/02 62/371 |
| 2008/0017774 A1 | * | 1/2008 | Jackson | ............. | A47G 23/0216 248/311.2 |
| 2013/0263622 A1 | * | 10/2013 | Mullen | ................. | F25D 11/003 62/451 |
| 2017/0102171 A1 | * | 4/2017 | Hall | ...................... | F25D 19/006 |

FOREIGN PATENT DOCUMENTS

| CN | 104819889 A | 8/2015 |
| EP | 1305608 B1 | 2/2007 |
| EP | 1228359 B1 | 9/2007 |

OTHER PUBLICATIONS

International Search Report and Written Opinion received for PCT Patent Application No. PCT/US2018/036966, dated Mar. 4, 2019, 16 pages.

\* cited by examiner

*Primary Examiner* — Frantz F Jules
*Assistant Examiner* — Lionel Nouketcha
(74) *Attorney, Agent, or Firm* — DLA Piper LLP (US)

(57) ABSTRACT

Systems and methods here may be configured for cooling and examining materials. In some example embodiments, the system may include a main thermoconductive body with indentations on the top surface, a bottom surface having legs structures along the edge, wherein the bottom surface and the plurality of leg structures form a partially enclosed bottom chamber, and a center channel connecting the top surface and the bottom chamber.

23 Claims, 16 Drawing Sheets

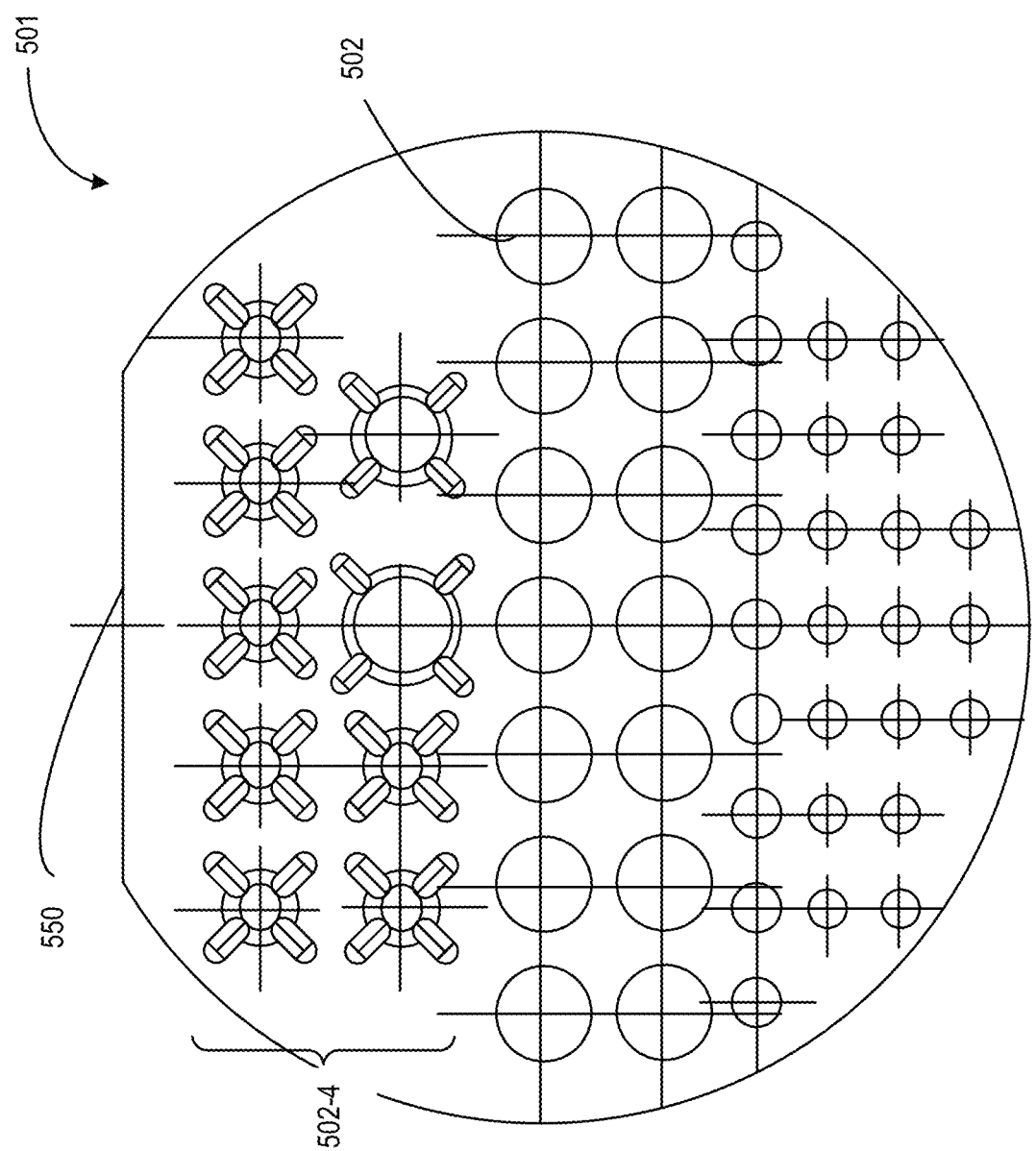

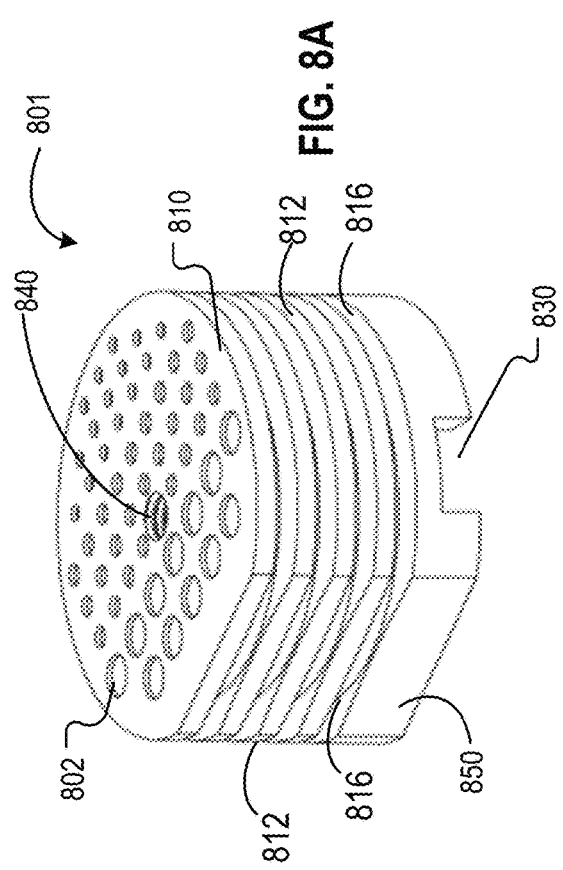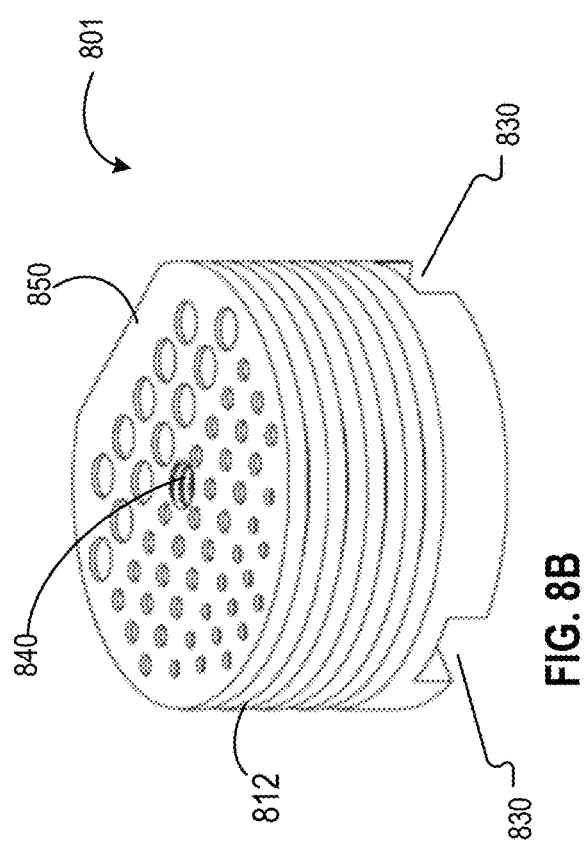

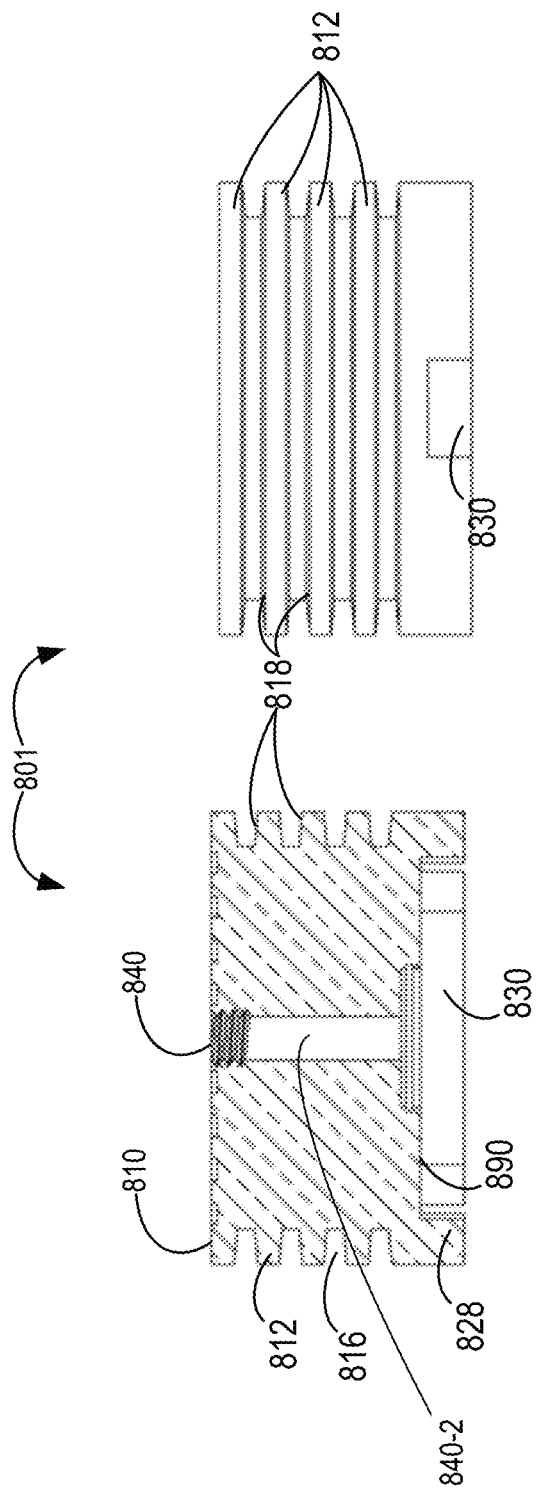

US 11,156,592 B2

UPFLOW COOLING STAGE FOR PHOTOLUMINESCENCE ANALYSIS

TECHNICAL FIELD

This application relates to the field of gemological cooling, staging, and analysis.

BACKGROUND

Previously, spectroscopic analysis and viewing of gemstones in ambient humidity and temperature conditions could cause irregularities and distortions in close up imagery and hinder analysis. Thus, it may be useful to cool gemstones and remove moisture around them in order to view and analyze them in conditions most suitable for analysis.

In some earlier embodiments, a cooling block was used to hold and cool gemstones for viewing and spectroscopic analysis. But such examples may have inherent features such as sample size and quantity limitations, inconsistent cooling, moisture and ice build-up on surface area of sample and cooling apparatus, and difficult maneuverability of cooling apparatus.

Thus, a technical solution is required to solve a technical problem: how to efficiently cool gemstones and minimize moisture and ice buildup in an easy to use mechanism that is conducive to analysis. The technical solutions presented herein, solve these technical problems.

SUMMARY

Systems and methods here may be configured for cooling and examining materials. In some example embodiments, the system may include a main thermoconductive body with indentations on the top surface, a bottom surface having legs structures along the edge, wherein the bottom surface and the plurality of leg structures form a partially enclosed bottom chamber, and a center channel connecting the top surface and the bottom chamber.

In some examples, the thermoconductive material is selected from the group consisting of a metal, a carbon-based material, a ceramic material, a thermal conductive composite, a thermal conductive polymer, an alloy, a silicate-based material, and combinations thereof. The cooling stage of claim 1, wherein the thermoconductive material comprises aluminum, gold, silver, copper, bronze, molybdenum, tungsten, beryllium oxide, aluminum nitride, silicon carbide, brass, iron, steel, nickel, carbon steel, lead, gallium nitride, zinc, tin, a tungsten carbide, graphite, cadmium, germanium, magnesium, monel, palladium, platinum, rhodium, tantalum, thallium, thorium, titanium, vanadium, a zinc alloy, a copper alloy, an aluminum alloy, a magnesium alloy, a nickel alloy, a beryllium alloy, and combinations thereof. In some examples, the indentations have flat bottoms for receiving a sample.

BRIEF DESCRIPTION OF THE DRAWINGS

For a better understanding of the embodiments described in this application, reference should be made to the Detailed Description below, in conjunction with the following drawings in which like reference numerals refer to corresponding parts throughout the figures.

FIG. 5B is a top down view of another example embodiment of the system described herein.

FIG. 8A is perspective view of an embodiment of the system described herein.

FIG. 8B is another perspective view of an embodiment of the system described herein.

FIG. 8C is a cutaway view of an embodiment of the system described herein.

FIG. 8D is a side view of an embodiment of the system described herein.

DETAILED DESCRIPTION

Reference will now be made in detail to embodiments, examples of which are illustrated in the accompanying drawings. In the following detailed description, numerous specific details are set forth in order to provide a sufficient understanding of the subject matter presented herein. But it will be apparent to one of ordinary skill in the art that the subject matter may be practiced without these specific details. Moreover, the particular embodiments described herein are provided by way of example and should not be used to limit the scope of the invention to these particular embodiments.

Overview

Figure 1A:
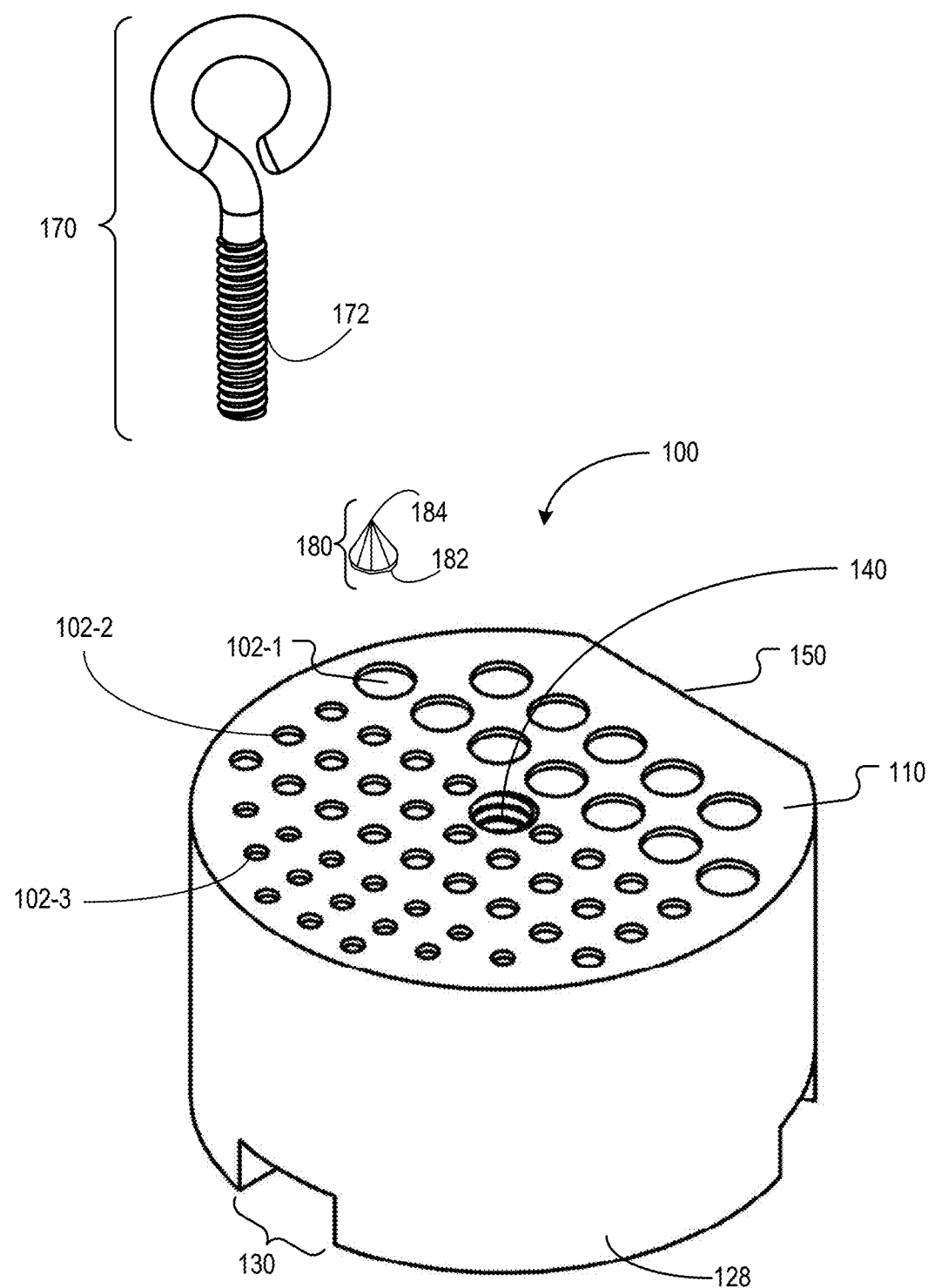
FIG. 1A is a perspective view of an example embodiment of the system described herein.

Systems and methods here may be used to position gemstones for observation. The positioning may include the use of a cooling block structure that is configured so as to overflow the gemstones with a liquid nitrogen film and purge the ambient atmosphere with cold nitrogen vapor to thereby remove any humidity or moisture on the gemstones. Such a system may allow for better viewing and analysis of the gemstones than if humidity or moisture are present and the gemstone is at ambient atmospheric temperature. In some examples, such a cooling block may be made of a material that has a high thermal conductivity. In such examples, the cooling block material may act as a heat sink for any object which comes in contact with it. In such examples, the material may quickly and easily change temperature by cooling, for example, if placed in a bath of liquid nitrogen, and then maintain those low temperatures. In some examples, such a cooling block may be moved or otherwise maneuvered by a user through use of a detachable transfer element such as a handle, or hook, or screw eye which may be utilized to minimize or prevent direct user contact with the cooling block itself. FIG. 1A shows an example cooling block 100 further described below.

Cooling Block Composition Examples

In some examples, a cooling block may be made of a material that has a high thermal conductivity. Below are listed various materials and combinations of materials that may be used to make such a cooling block. It should be noted that the lists below are not intended to be limiting. Any of various combinations of materials listed below or otherwise, may be used to make up the block, to plate or clad the block, and/or to make portions of the block.

In some examples, the cooling block body 100 may be made from a single piece of metal such as but not limited to, copper, gold, aluminum, molybdenum, tungsten, silver, bronze, beryllium oxide, aluminum nitride, silicon carbide, brass, iron, steel, nickel, carbon steel, lead, gallium nitride, zinc, tin, a tungsten carbide, graphite, cadmium, germanium, magnesium, monel, palladium, platinum, rhodium, tantalum, thallium, thorium, titanium, vanadium, a zinc alloy, a copper alloy, an aluminum alloy, a magnesium alloy, a nickel alloy, a beryllium alloy, and any combinations thereof. In some examples, the cooling block may be made of another material such as diamond or other carbon form. In some examples, the block may be made of a combination of any of these materials listed in this paragraph and/or other materials. In some examples, the cooling block may include layers of material such as an outside coating or plating of one or more of these materials listed in this paragraph. In some examples, layers of material may be sandwiched together to form the cooling block. In some examples, the thermal conductivity of the material is over 30 or 50 W/m K.

In some examples, the block may be made of a metal matrix composite with ceramic particles such as MN and silicon carbide SiC. In some examples, an aluminum matrix composite may be used. In some examples, a copper matrix composite may be used with fillers such as carbon, tungsten, molybdenum, and/or Invar. In such examples, carbon fibers with a diameter of around 10 μm may be used with copper to form a matrix material for the cooling block 100. In some examples, the carbon fiber copper matrix composite may be made by coating carbon fibers with copper and then diffusion bonding. In some examples, diffusion bonding may be sintering.

In some examples, copper may be used with silicon carbide, titanium diboride (TiB2) and/or alumina. In using aluminum with copper, a powder metallurgy may be used because of the difference in melting points. In such examples, a copper alloy may be used, such as Cu—Ag, to reduce the melting temperature. Such a method may include coating the matrix metal on the filler units, followed by pressing and sintering. Thus, mixing the metal powder and coated filler is not necessary. In some examples, a Beryllium-matrix composite may be used.

In some examples, a carbon matrix composite may be used. In such examples, a carbon fiber may be used with a carbon, making a carbon-carbon composite. Such carbon-carbon composites may be made by making a pitch-matrix or resin-matrix composite and subsequent carbonization of the pitch or resin to form a carbon matrix composite. After carbonization, the carbon matrix may be porous so pitch or resin may be impregnated into the composite and then carbonization is conducted again and repeated to reduce the pores. In some examples, graphitization may follow carbonization by heating to 2000-3000 degrees C.

In some examples, a carbon and graphite composite may be made by consolidating oriented precursor carbon fibers without a binder and subsequently carbonizing and/or graphitizing. In some examples a pyrolytic graphite may be encased in a structural shell. In some examples, a pitch-derived carbon foam may be used.

In some examples, a ceramic matrix composite may be used. Such examples may include an SiC matrix composite made from a carbon-carbon composite by converting the matrix from carbon to SiC [65]. Chemical vapor deposition may be used with AlN or Si. In some examples, an SiC-matrix metal (Al or Al±Si) composite, as made by a liquid-exchange process, may be used.

In some examples, a borosilicate glass matrix may be used (4.1 at 1 MHz for B2O3-SiO2-Al2O3-Na2O glass). Tape casting may be used, followed by sintering. Another example is aluminum nitride with interconnected pores (about 28 vol. %), the composites of which are obtained by glass infiltration to a depth of about 100 μm.

In some examples, the composites may be made using chemical vapor infiltration in which carbonaceous gas is used to infiltrate the composite and decompose to form carbon.

Structure Examples—Top

In some example embodiments, the main structure cooling block is shown in example FIG. 1A. In FIG. 1A, the main cooling block 100 is generally shaped as a cylinder with a top surface 110 and a flat edge 150. It should be noted that a cylinder is not the only shape the cooling block 100 could take, it could be any number of shapes including but not limited to a cube, pyramid, sphere, or other shape. The example of FIG. 1 as a cylinder preferred embodiment is not intended to be limiting, and the term block is not intended to convey any particular shape.

In the example of FIG. 1A, the cooling block 100 includes various indentations or impressions 102 on its top surface 110. In some examples, these indentations or impressions 102 may be considered open faced compartments. These indentations 102 may be of various sizes, for example, relatively larger sizes 102-1, medium sizes 102-2 and/or smaller sizes 102-3. Any combination of these or other sized impressions 102 may be configured into the surface 110 of the block 100 including configurations with the same sizes. In some examples, the larger sized indentations are flat bottomed and circularly/cylindrically shaped on the surface 110 of the cooling block 100. In such a way, the flat bottomed circular indentations may hold a gemstone 180 in place by its table or crown 182, with the culet or pavilion 184 facing or pointing up and away from the block 100 top surface 110. In some example embodiments, the diameters of these circular indentations 102 could be 4 mm for the large 102-1, 2 mm for the medium 102-2, and 1.5 mm for the small 102-3. In some examples, the depth of the indentations 102 could be 0.5 mm from the surface 110 of the block 100. In some examples, the depth may be between 0.1 and 0.7 mm.

In some examples, as shown in FIG. 1A, a center hole 140 is set in the middle, or approximate middle of the block 100.

In the example of FIG. 1A, the center hole 140 includes internal threads which may mate with matching threads 172 in a hook, or handle, or screw eye 170. In some examples, this center hole 140 runs through the entire height of the block 100. In use, the user could screw the handle 170 into the center hole 140 in order to move and manipulate the block 100 without touching or handling the block 100 directly. In cases where the block 100 is cold due to the liquid nitrogen bath, (see FIG. 6) this handle 170 allows users to avoid freezing their hands. It also allows for a removable but precise way to maneuver the block 100. In some examples, the handle 170 may be referred to as an eyebolt or screw eye and be made of stainless steel such as type "316" stainless steel.

Also shown in the example block 100 of FIG. 1A are castellated feet 128 with alternating spaces, arches, gaps, cut outs, voids, or otherwise indentations 130 which run around the circumference of the block 100 and define individual leg structures 128. In some examples, these indentations 130 on the base of the block 100 may provide room for material to move under the block 100 as discussed below. In some examples, the block 100 includes three feet 128 and three arches 130. In some examples, four feet 128 and four arches 130 may be used. The number of feet 128 and arches 130 may differ in various embodiments, with the configuration allowing material to move under the block 100.

In some examples, the channel 140 has a diameter that is between 5% and 10% of the diameter of the main body or block 100. Some examples have diameters of the stage at 1⅝ inches (41.3 mm) and the hole diameter is 5/32 inches (4 mm) (approx. 10%) Thread size in the center channel may be 140-1 from FIG. 3A may be #10-24 and 0.16 inches deep in some example embodiments. Other various sizes or combinations of sizes may be used in various embodiments, and these examples are not intended to be limiting.

It should be noted that the center hole or channel 140 in FIG. 1A may not necessarily be the only hole or channel that is in an example cooling block 100. In some examples, more than one hole or channel may be configured in a block 100. In some examples, multiple holes may be positioned in various places around the block and allow for similar nitrogen bubbling as described in FIG. 6. Such holes may be arranged in an annular configuration around the outside of the block 100. In some examples, three holes may be configured in an equally spaced triangular shape around the rim of the block 100. In some examples, four holes may be placed in a diamond or square corners positions around the outside of the block. In some examples, holes in the center of the block may be configured with holes around the outside of the block as well. Any combination of these or other hole configurations may be used as described herein.

It should be noted that the center hole or channel 140 may take any of various shapes. It need not have a circular cross section. The center hole or channel 140 may have a cross sectional shape of, but not limited to, a circle, an oval, a polygon with 3 or more sides, a triangle, a square, a rectangle, a diamond, a pentagon, a hexagon, a heptagon, an octagon, and/or an irregular shape. In such examples, the handle 170 may have a corresponding shape and complementary ability to fasten, hook, latch, friction fit, or otherwise attach to the block 100.

Figure 2A:
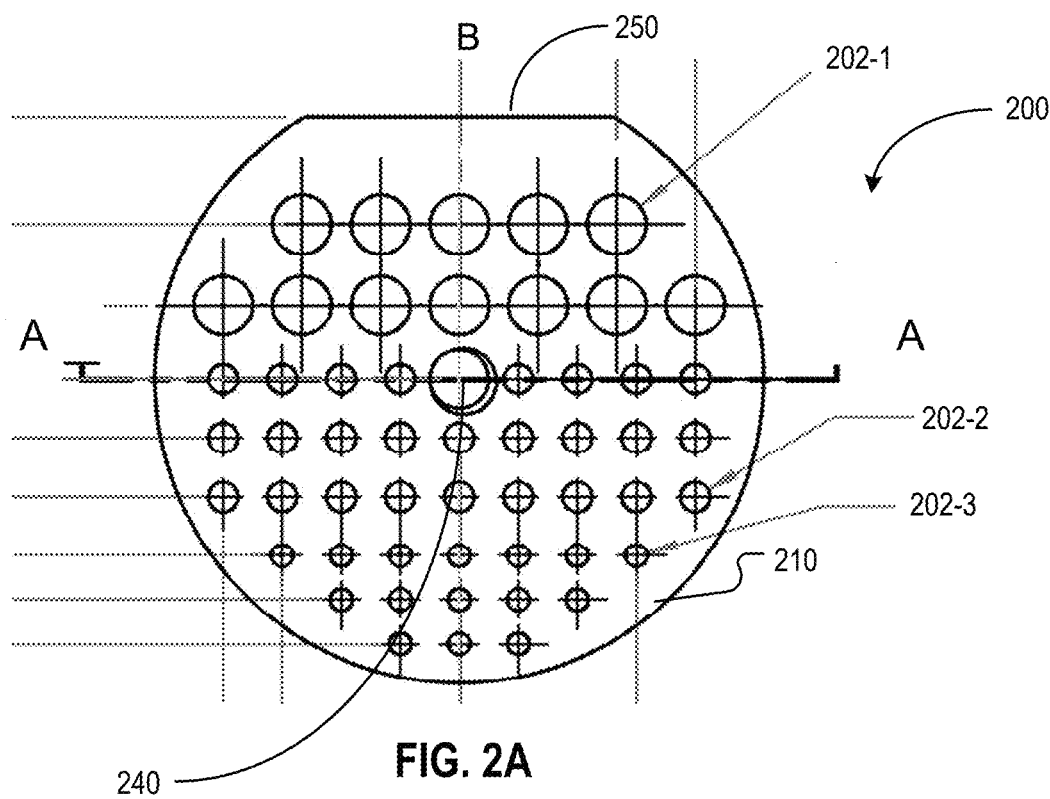
FIG. 2A is a top down view of an example embodiment of the system described herein.

FIG. 2A shows an example view from the top surface 210 of the cooling block 200 with center line A running from left to right and center hole 240. In the example of FIG. 2A, an example arrangement of indentations 202 are shown on the block surface 210 but such an example is not intended to be limiting. Any arrangement of indentations may be formed in the top surface 210 of the block 200.

In the non-limiting example of FIG. 2A, twelve larger indentations 202-1 are arranged in two rows on the block 200 surface 210. In the example shown, the center of the farthest row of large indentations 202-1 is 10.5 mm from the center A of the block 200 top surface 210. In the example shown, the closer to the center A row of large indentations 202-1 is 5 mm from the center A. In the example of FIG. 2A, the three rows of medium indentations 202-2 may be arranged in three rows on the block 200 surface 210 with the middle of one row running down the center A of the block and the next two rows of medium indentations 4 mm away from the center A as measured from their centers, making the center of the third row of medium indentations 202-2 a total of 8 mm away from the center A. In some examples, fifteen small indentations 202-3 may be arranged in three rows on the surface 210 of the block 200. In some examples, the centers of the smaller indentations 202-3 are 12 mm, 15 mm, and 18 mm, respectively from the center A of the block surface 210.

In some examples the indentations are evenly spaced from another center line B running from top to bottom of the example block 200 of FIG. 2A. In such examples, the spacing of the rows of indentations 202 may be such that each indentation is spaced evenly from one another to allow for easier viewing. For example, the centers of the small 202-3 and medium indentations 202-2 may each be set 4 mm from the vertical centerline B. In some examples, the centers of the farthest large indentations 202-1 may also be 16 mm from the center B but the second set away from the center B may only be 10.7 mm away due to the larger diameter of the larger set of indentations 202-1.

It should be noted that these sizes, arrangement, and numbers shown in FIG. 2A are not intended to be limiting but merely examples of how the indentations 202 are arranged.

In use, these indentations 202 serve as receptacles for any of various gemstones which may be placed, one inside each indentation, with the table or crown, on the flat surface of the indentation 202 so the culet or pavilion faces or points up as shown in FIG. 1A. Due to the various sizes of indentations 202, various sizes of gemstones may be loaded into the cooling block 200 top surface 210 indentations 202 for viewing.

Photoluminescence Spectroscopy, and/or UV-Vis Spectroscopy may be performed with the gemstone samples inside the compartments/indentations 202. Analysis could be performed using an optical probe or microscope objective such as in optical microscopy. Altering the design for table up analysis is an alternative design option. Such an alternate design would include indentations 202 that allow for the gemstone culet or point to be placed into the indentation and the table and crown to face upward, from the surface of the block 200 as described in FIG. 1B-1E.

In some example embodiments, the cooling block 200 includes a flat portion 250 which is a removed portion or arc of the cylinder shape of the block 200. In such examples, such a flat portion 250 may be used for alignment purposes by the user of the block 200. By making one portion of the otherwise cylinder-shaped block 200 look distinct, and able to be easily aligned, the rows of the indentations 202 can be aligned as well, and each gemstone can be mapped, cataloged, or otherwise plotted on the surface 210 of the block 200.

Referring back to FIG. 1B shows an alternate design that allows the block 101 to hold larger samples in a table up configuration, and could accommodate many sample sizes simultaneously with differently sized indentations 102. The optional indentations 102-4 shown in the example of FIG. 1B could be cone shaped or cylinder shaped with beveled edges and slits to accommodate a variety of gemstone cuts and sizes. In such a way, the beveled edges and slits on the indentations may hold a gemstone 180 in place by its culet or pavilion 184 with the table or crown 182, facing or pointing up and away from the block 101 top surface 110.

Figure 1B:
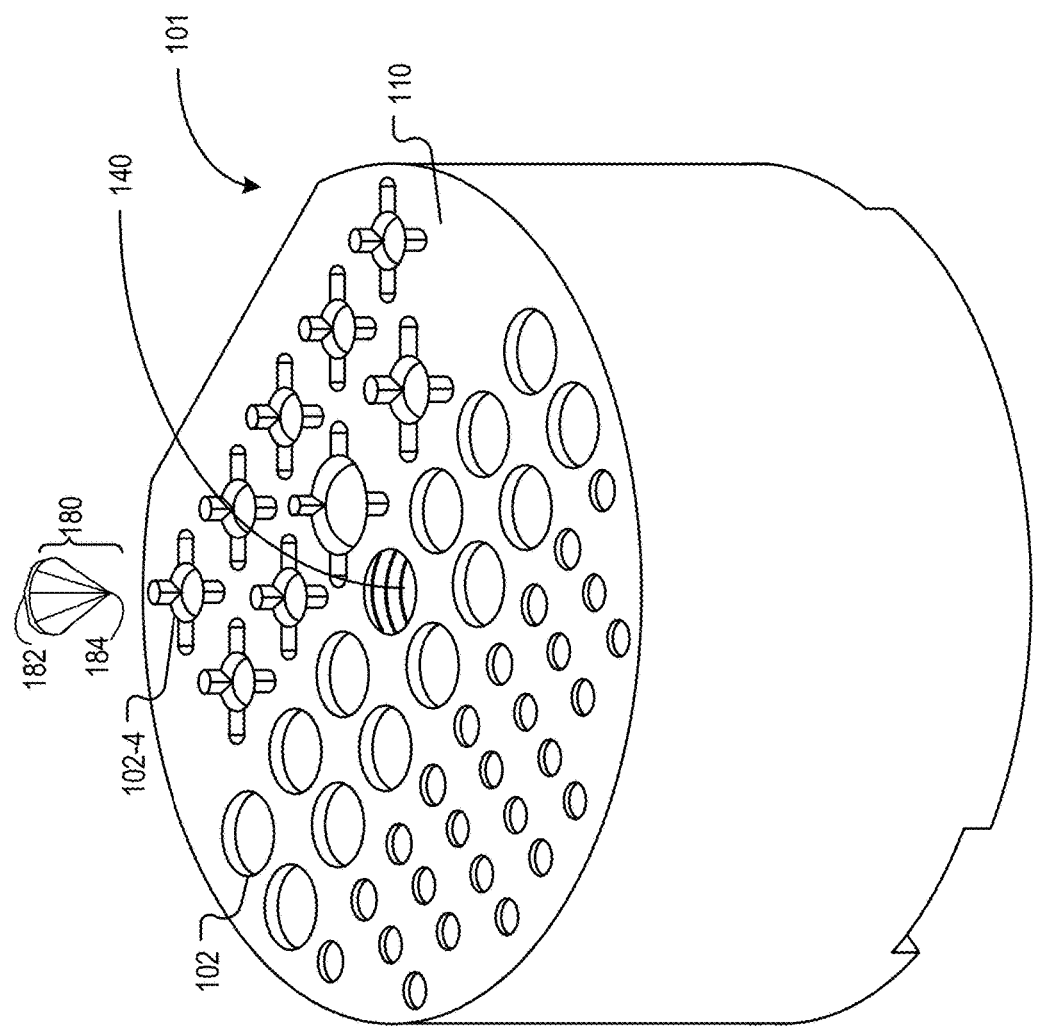
FIG. 1B is a perspective view of another example embodiment of the system described herein.
Figure 1C:
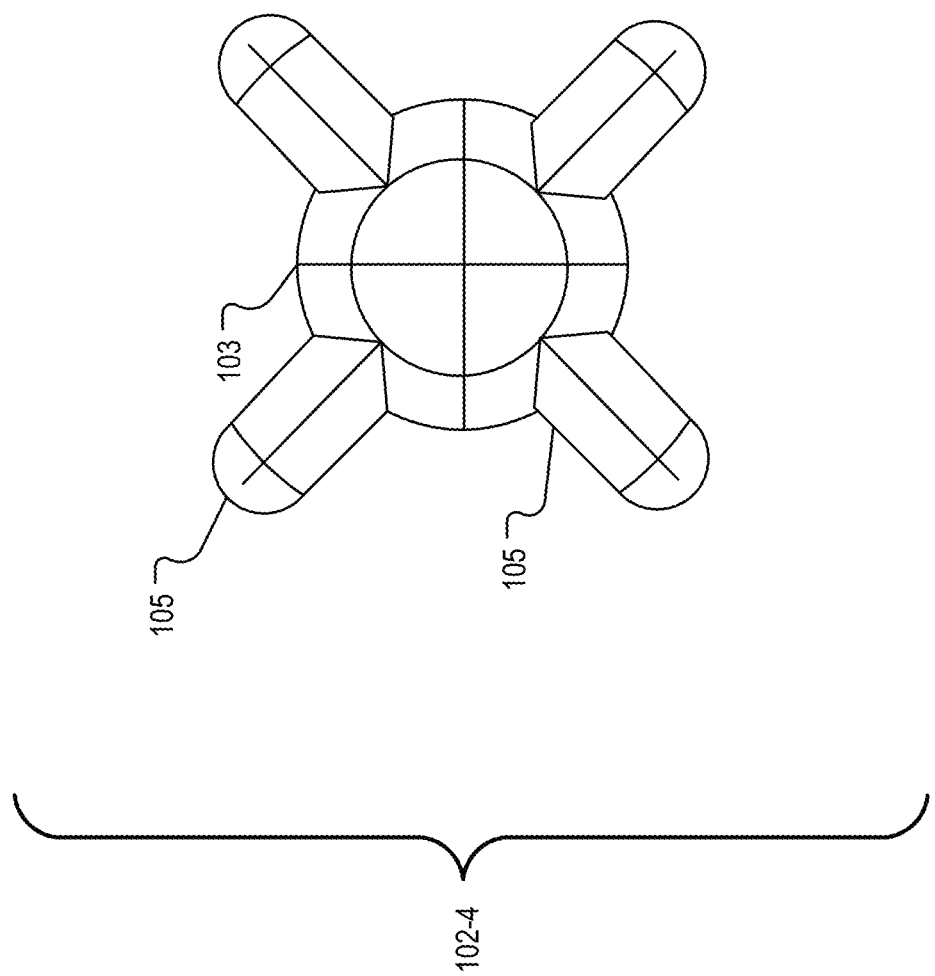
FIG. 1C is a detail view of FIG. 1B example embodiment of the system described herein.

A detail of these optional slits and bevel features are shown in FIG. 1C. FIG. 1C shows a detail top down view of the optional indentations 102-4 with beveled edges 103 and slits 105. These beveled edges 103 could allow for gemstones of many various sizes to be positioned in the indentations on the surface of the block with culet and pavilion side down, table side up, depending on the sizes of the slits. In such a way, the angles of the pavilion facet junctions may be supported, and the gem may sit table side up, and culet down in the indentation 102-4, above the surface of the block.

The slits 105 in example FIG. 1C are shown as beveled channels that cut into the surface of the block and provide a four corner surface on which gemstones of various sizes could be placed. In some example embodiments, the slits 105 are four per indentation 102-4. In some examples, different number of slits 105 are included in each indentation 102-4. For example, an embodiments may include three slits 105 per indentation 103-4. In some examples, only two slits 105 may be arranged per indentation 102-4. In some examples, five slits 105 may be included in each indentation 102-4. Any number of slits could be used in various sizes to accommodate various gems and culets, including any combination of those described above.

In some example embodiments, these beveled edges 103 and slits 105 for the indentations 102-4 may allow for liquid and/or gaseous nitrogen or other coolant to better surround the features of the gemstones placed into the indentations 102-4. In such examples the slits 105 may act as channels for the liquid and gaseous nitrogen to move around the gemstones and surround the various aspects of the gemstones, to better cool them and remove moisture as described herein. In some examples, the slits 105 may hold the stone away from the edges of the indentation 102-4 and thereby allow liquid and gaseous nitrogen to flow around the stones. Further, the slits may allow the liquid nitrogen to off-gas and relieve pressure if the liquid nitrogen gets trapped in bottom of the indentation 102-4. The off gassing reduces shaking of the gem and stabilizes the gem for analysis.

Some embodiments add additional features to help with the circulation of coolant such as liquid and gaseous nitrogen. FIG. 1D shows an example embodiment where the larger indentations 102-4 include slits for larger sample gemstones. In the example shown, additional holes 190 are integrated in the side wall 150 and indentations 102-4 in order to facilitate the circulation of gaseous and liquid nitrogen around the gemstones. Such circulation may aid in cooling but also alleviate pressure differences from above and below the sample gemstones placed in the indentations 102-4. In some examples, these holes 190 may be circular and lead into the bottom or side wall of the indentations 102-4. In some examples, these holes 190 may be slits or channels cut into the block 103 and match up to the indentations 102-4.

Figure 1E:
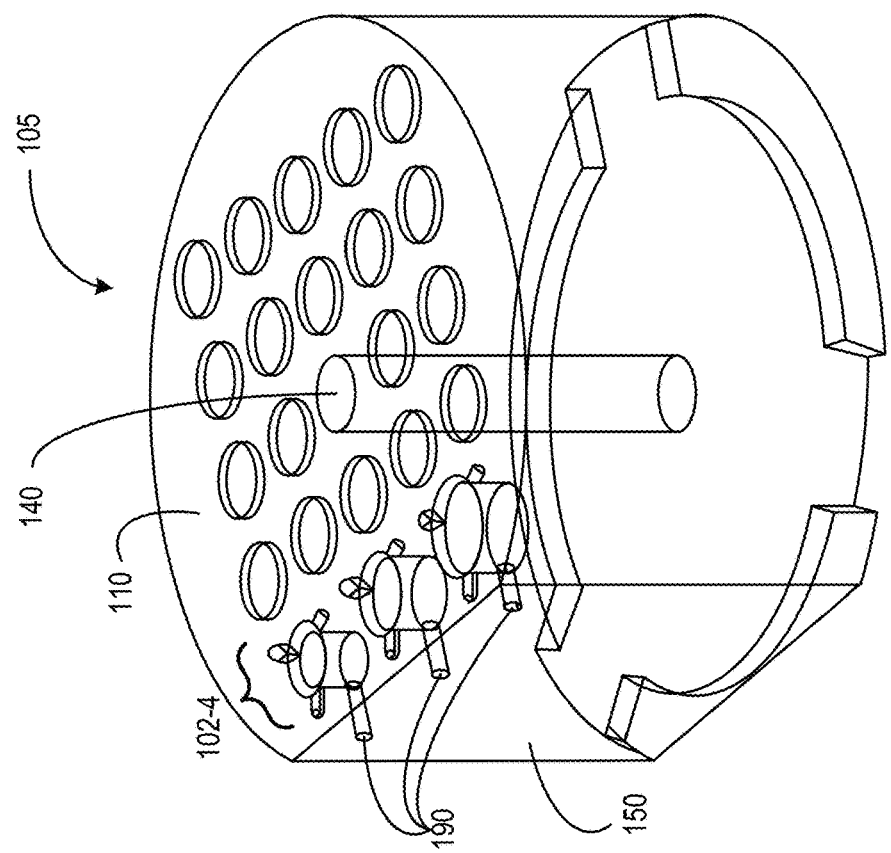
FIG. 1E is a transparent perspective view of an embodiment of the system described herein.
Figure 1D:
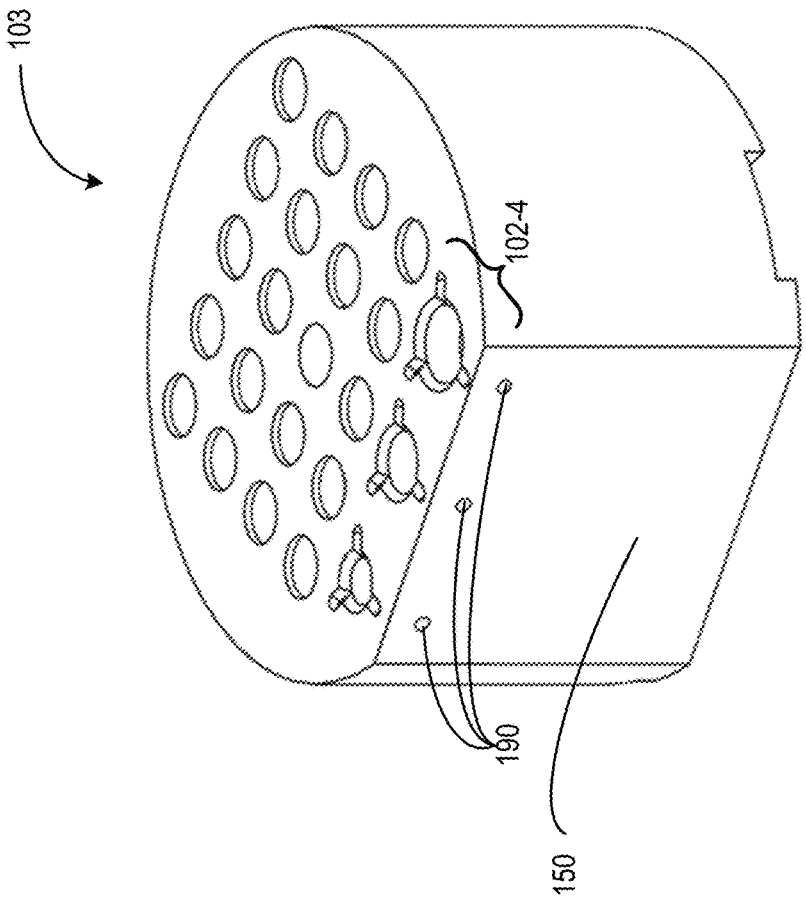
FIG. 1D is a perspective view of an embodiment of the system described herein.

FIG. 1E is a perspective view of the block 105 as in FIG. 1D but in a transparent manner, showing the interior surfaces of the block including the internal center channel 140 as well as the holes 190 cut into the side of the block 105 that connect to the bottom or side walls of the indentations 102-4 in the top table 110 of the block. As can be seen due to the transparent diagram, the holes 190 that connect to the indentations 102-4 may allow material such as cooling material like liquid nitrogen and nitrogen gas to flow around and through the indentations and through the side wall 150 of the block. It should be noted that the holes 190 are described as circular holes but could be any shaped channel, hole, slit, or other surface. The holes 190 need not be circularly shaped as shown in FIG. 1D and FIG. 1E, they could be slits, square holes, triangularly shaped holes, or other shape. Additionally or alternatively, each indentation in 102-4 need not have only one hole but could have multiple holes connecting to the outside surface 150 or to other indentations 102-4 or central channel 140 or any combination of these.

Structure Examples—Bottom

Figure 2B:
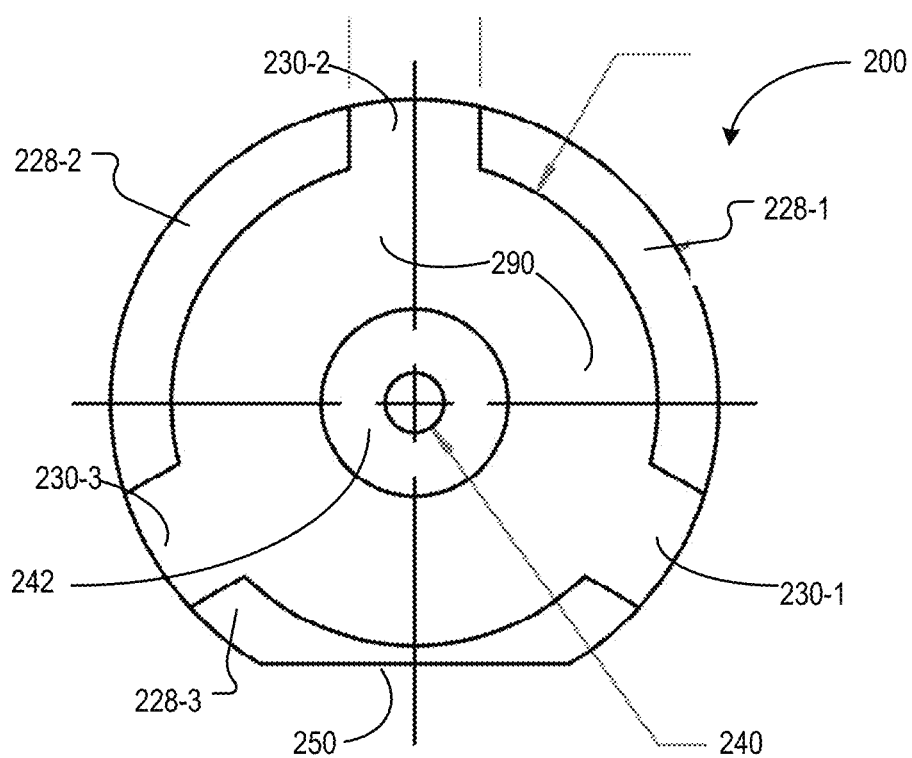
FIG. 2B is a bottom up view of an example embodiment of the system described herein.

Certain example embodiments of the cooling block 100 described herein may include certain features on the bottom of the block, opposite the top surface 110. FIG. 2B shows a bottom perspective of the block 200 with some example features. In FIG. 2B, the bottom of the cylindrically shaped cooling block 200 may be divided into an outer rim of castellated leg structures 128 separated by spaces, arches, cut outs, voids, or otherwise indentations 230. In some example embodiments, the number of leg structures 228 may be three, corresponding to three arches 230. Thus, for example, one leg 228-1 may be positioned evenly spaced from the second 228-2 and third 228-3 legs, by corresponding arches 230-1, 230-2, and 230-3. In some example embodiments, these legs may be 8.3 mm thick, in other words, the legs may have the same outside edge as the cooling block itself 200 and be approximately 8 mm thick with a circumference which inside the outside, forming a rim around the cylindrically shaped cooling block 200. In some examples, the arches 230 may be evenly spaced and around 9 mm wide. In some examples, the arches may be 8.9 mm wide. In some examples, the arches 230 may be between 7 and 9 mm wide. In some examples the arches 230 may be between 8.4 and 9.5 mm wide. In some examples, the arches 230 are between 3 and 5 mm tall, cut into the height of the block 200. In some examples, the arches are 4 mm tall, making the legs 228, 4 mm tall as well.

In some examples, this rim of legs 228, spaced apart by arches 230 may interconnect a raised bottom portion 290. In other words, the example arches 230 may be the same height as a raised bottom 290 of the cooling block 100 which is then held up by a rim of leg 228 portions. In some examples, this rim of legs 128 may be three legs. When the example cylinder cooling block 200 is placed on a flat surface, the legs 128 hold the cylinder block up and the arches 230 and raised bottom 290 thereby form a void or chamber under the cooling block 200. In some example embodiments, the block 200 includes a center hole 240 which runs all the way through to the cooling block to the top surface 210. In some examples, this center hole 240 is 4 mm in diameter. In some examples, it is between 3 and 5 mm in diameter. The bottom chamber 290 has a height that is between 5% to 10% of the height of the main body or block 200.

Internal Feature Examples

Figure 3A:
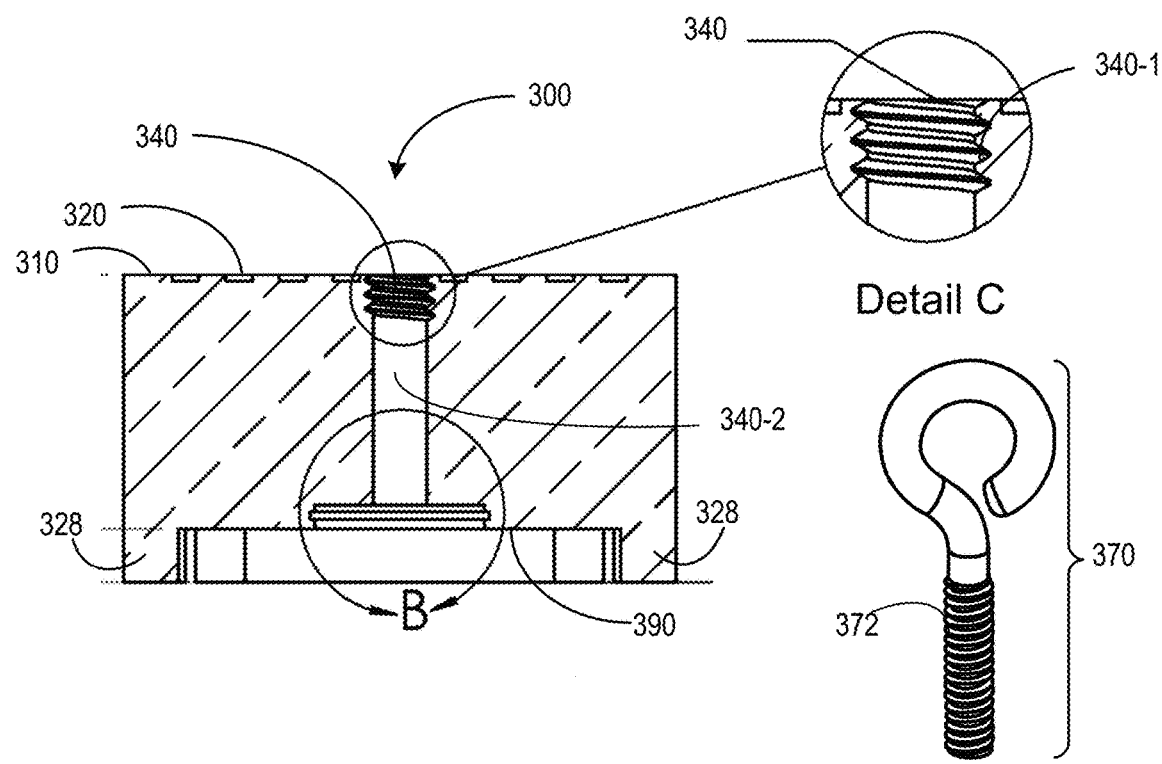
FIG. 3A is a cut away view of an example embodiment of the system described herein.

FIG. 3A shows an example cut away view of the inside of the cylindrically shaped cooling block 300. In the example cut away view, the indentations 320 are visible along the surface 310 of the block 300. Also visible is the raised bottom 390 and the legs 328. Also visible in the cut away view of FIG. 3A is the center hole 340 running from the top surface 310 to the bottom 390, all the way through the center of the block 300. In some examples, the center hole 340 may be considered a channel connecting the surface 310 and bottom 390. In the example of FIG. 3A, the top of the center hole 340 includes threads 340-1 which may interact with some sort of transfer element such as a handle or hook 370 with corresponding threads 372 or mating screw threads. In such a way, the block 300 may be transported or moved by a handle or hook 370 without having to touch the block 300 itself, but by merely screwing in a handle or hook 370 by the threads 340-1 in the center hole 340. Such a block structure 300 and handle 370 arrangement would allow for a user to move or transport the block 300 without having to directly touch or handle it. In examples where the block 300 is cooled by liquid nitrogen, such a removable handle 370 would protect a user from the cold. In the example, the center hole 340 also includes a main shaft 340-2 below the threaded portion 340-1. In some examples, the entire length of the center hole 340 may be threaded, and in some examples, only a portion of the center hole 340 may be threaded 340-1.

Figure 3B:
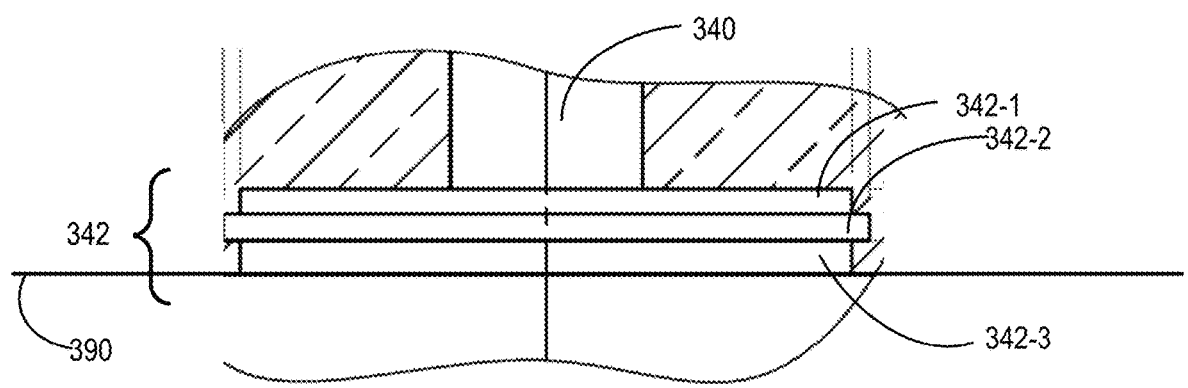
FIG. 3B is a detail view of FIG. 3A, which is a cut away view of an example embodiment of the system described herein.
Figure 3C:
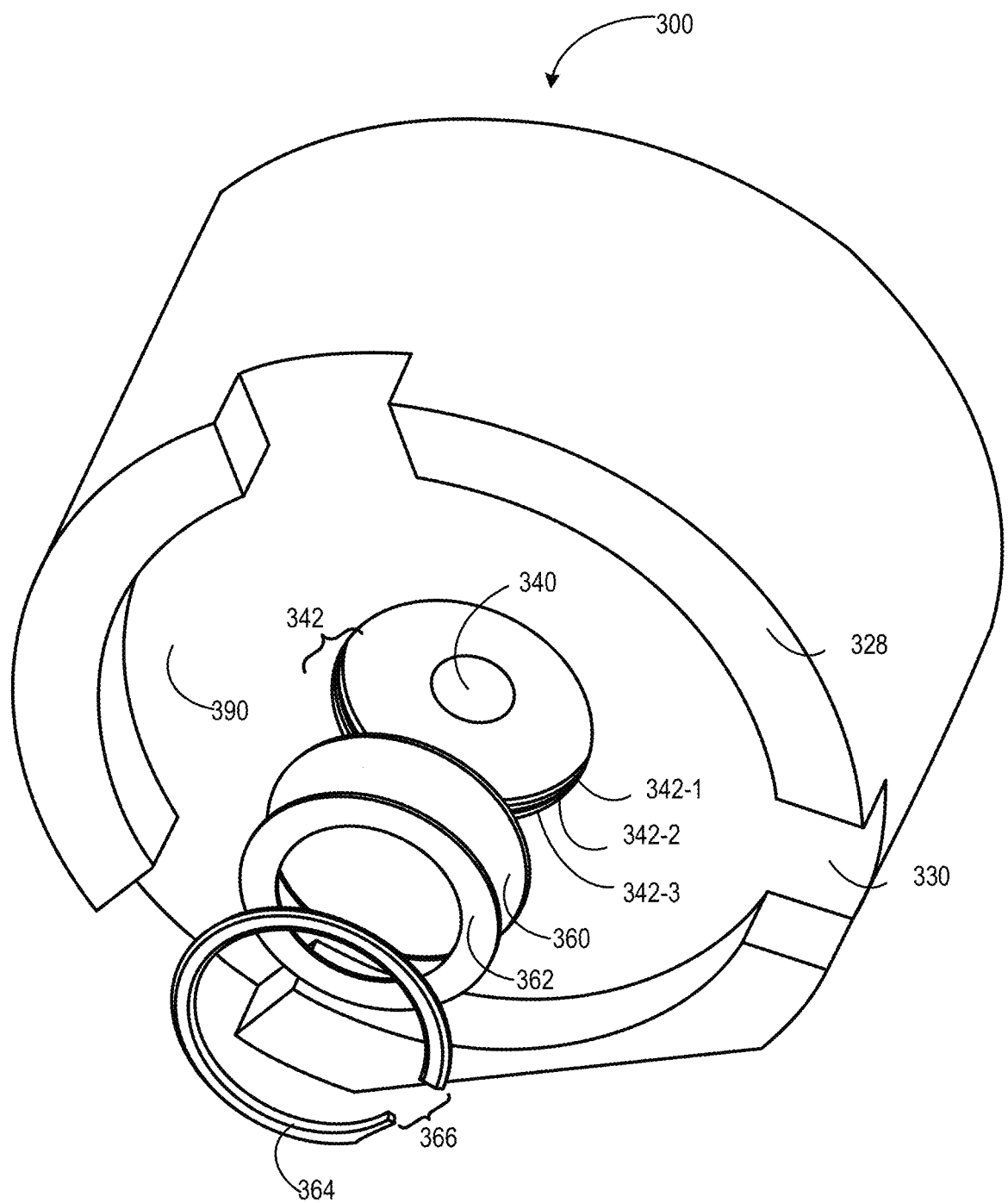
FIG. 3C is a perspective view of FIG. 3A, which is a cut away view of an example embodiment of the system described herein.

FIG. 3B shows a side cut away detail view of FIG. 3A. In some example embodiments, the inlet to the center channel 340 from the underside 390 includes structures 342 that are cut from the bottom 390 of the block 300 and are configured to hold or retain a filter 342-1 in place. In some example embodiments, the filter may be held in place to the bottom 390 of the block 300 by a washer and a retention clip. FIG. 3C shows an exploded view of these features.

In some example embodiments, a portion 342 is cut into the raised bottom 390 around the center hole 340, but with a larger diameter than the center hole 340 and may form a recessed portion or more than one recessed portion 342 in the block 300 in order to accommodate various features such as a filter. Other such portions 342 may be cut or formed from the bottom 390 of the block to retain, hold or otherwise secure a washer. Such a washer may require a slightly larger diameter recess 342-2 than the recess holding the filter 342-1 such that the washer would overlap the edge of the filter 342-1 and still not block the filter. In some example embodiments, a third recess 342-3, with a diameter less than that for the washer 342-2 and closer to if not the same as the diameter of the recess for the filter 342-1 may be used to secure a retention ring. Such a retention ring may be circularly shaped that is secured in the circumference of the recessed portion 342-3 with a spring force that holds it into position in the recess 342-3. Another detail of such retention ring is shown in FIG. 3C.

In some examples, this recessed portion 342 is circularly shaped and between 12 and 13 mm in diameter. In some examples, this recessed portion 342 is 12.7 mm in diameter. In some examples, the recessed portion 342 includes more than one diameter recessed at different depths 342-1, 342-2, 342-3. In such examples, the first 342-1, 12.7 mm diameter recess may be 0.5 mm deep and a second recess 342-2, is 13.4 mm in diameter and cut 0.6 mm deep. In some examples, the second recess 342-2 may be between 13 and 14 mm in diameter.

Within these recessed portions 342-1, 342-2 and 342-3, as shown in FIG. 3B and also FIG. 3C, any of various washers, retention clips, filters, caps, and/or retaining bolts may be used to secure a filter 360 or other device which is mounted near or over the center channel 340, this filter 360 may filter material such as ice from the liquid nitrogen as liquid nitrogen flows up through the center channel 340.

In any embodiment described herein, the filter 360 may be a Wire Mesh such as Type "316" Stainless Steel Wire Cloth Disc. In any embodiment, the mesh and wire size could vary, for example, it could be Mesh 20×20 with a wire diameter of 0.016 inches, Mesh 40×40, with a wire diameter of 0.010 inches, and/or a Mesh 100×100, with a wire diameter of 0.0045 inches. These or any other sized filter mesh could be used.

FIG. 3C shows a perspective underside view of FIG. 3A. In FIG. 3C, the underside of the block 300 is shown with a filter 360 washer 362 and retention clip 364 holding the filter 360 in place. As described in FIG. 3B, the three recessed portions 342 in the underside 390 of the block 300 may have circumferences that correlate to the filter 360, washer 362 and retention ring 364. For example, the deepest recessed portion 342-1 may be the same circumference or just slightly larger circumference as the filter 360 such that the filter may be placed into the recess 342-1 and cover the center channel 340. Then, a washer 362 may be fit in over the filter 360 in a recess 342-2 that is slightly larger in diameter than the recess for the filter 342-1. In such a way, the washer 362 may cover the edge of the filter 360 and even overlap the edge of the filter 360. In some example embodiments, this larger diameter recess 342-2 may serve as its own way to secure the washer 362 which may have a circumference the same as or slightly smaller than its respective recess 342-2 such that it may fit into the recess 342-2 and form a seal. In some example embodiments, the recessed portions 342 are the same diameter and even the portion that the washer 362 fits into is the same. In such examples, only the retention ring 364 may hold the washer in place, not the recessed portion 342-2 itself. In some embodiments, the washer 362 may be stainless steel, such as type "316" stainless steel or any other material, such as but not limited to rubber, plastic, latex, and/or polyurethane, or any combination of these and the retention ring 364 may also be stainless steel such as 18-8 stainless steel or any other kind of material.

In some example embodiments, a third recessed circumference 342-3 is formed in the bottom 390 of the block 300. In some example embodiments, this third recessed portion 342-3, has a circumference slightly smaller than that for the washer 342-2. In such a way, a lip may be formed to help secure the washer 362 in its respective recess 342-2. In some example embodiments, the recessed portion 342 is the same circumference and only the retention ring 364 holds the washer 362 and filter 360 in place.

In some example embodiments, the retention ring 364 is a spring force element that may be deflected to fit into its respective recess 342-3 but only by slight bend or deflection of the ring 364. The ring 364 may not be completely formed, and a gap 366 in the ring 364 may allow it to be bent slightly and then retain a spring expansion force. In such examples, the retention ring may exert a force against the walls of its recessed portion 342-3 and thereby hold itself in place. In such examples, the retention ring 364 may thereby hold the filter 360 and in some example embodiments the washer 362 in place as well. In some examples, the retention ring 364 may be made of metal such as aluminum or steel, or rigid plastics capable of being slightly deflected, yet be rigid enough to impart a return spring force that may act to retain the retention clip 364 in place.

In some examples, a third layer of recess 342-3 is cut into the bottom raised portion 390 of the cooling block 300 around the center hole 340. In some examples, this third recess 342-3 may be 0.7 mm deep and 13.4 mm in diameter. In some examples, the third recess 342-3 may be between 13 and 14 mm in diameter.

Alternative or Additional Block Embodiment Features

Figure 4:
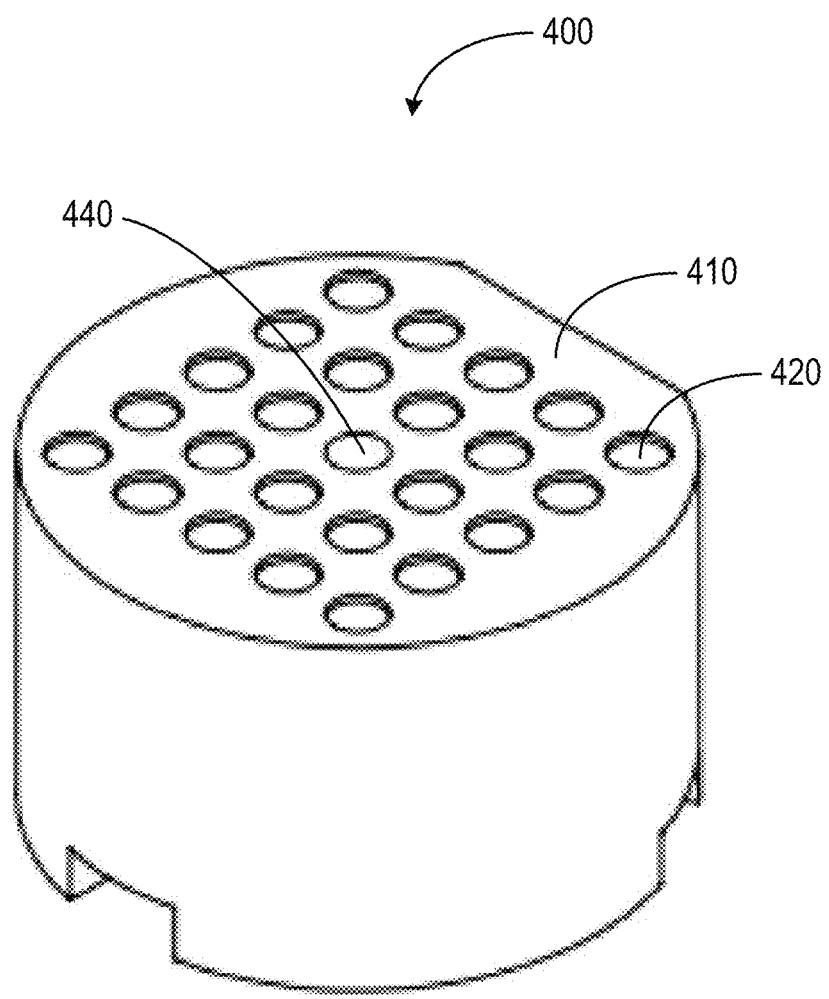
FIG. 4 is a perspective view of another example embodiment of the system described herein.

In some examples, the cooling block may be configured with a different arrangement of indentations 420 than that shown above. FIG. 4 shows an example block 400 with 24 indentations arranged in rows and columns, evenly spaced on the surface 410 of the block 400. The center hole 440 is shown where one of the indentations may otherwise be placed. The indentations 420 in this example are uniformly shaped and distributed on the block 400. Other embodiments or combinations may include various arrangements of indentations 420.

Figure 5A:
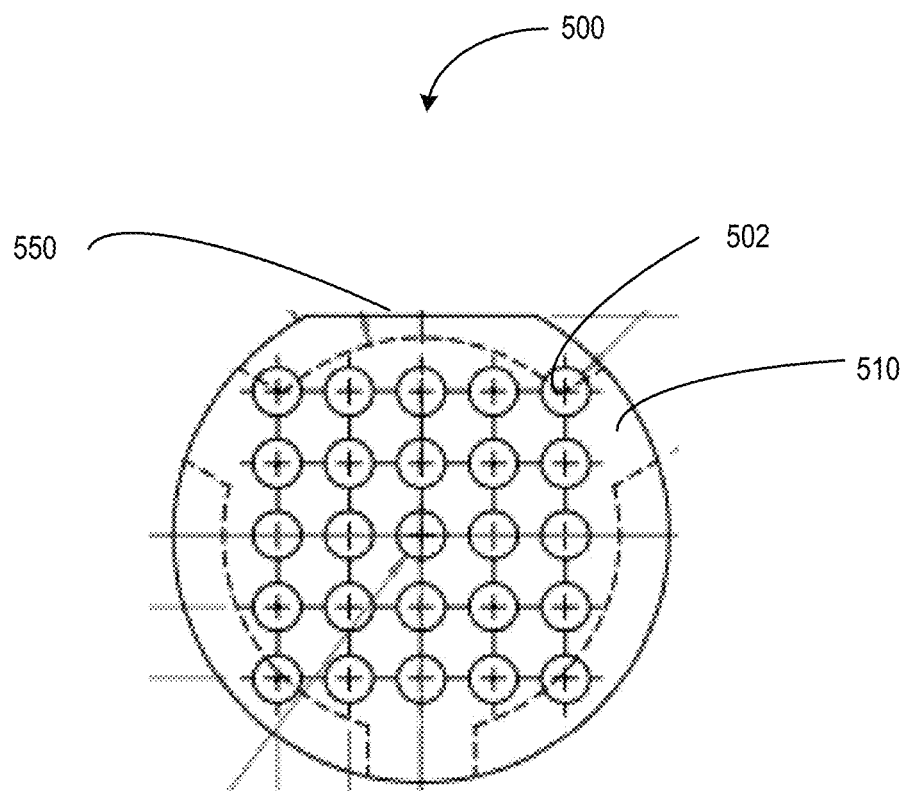
FIG. 5A is a top down view of an example embodiment of the system described herein.

FIG. 5A shows a top down view of the example block 500 from FIG. 4 with flat portion 550 and five rows and five columns of evenly spaced indentations 502 on the block surface 510. The center hole 540 is shown where one of the indentations 502 would otherwise be located.

FIG. 5B shows a block 501 example, with additional or alternative features, from a top down view of the example block from FIG. 1B with flat portion 550 and the indentations cylinder shaped indentations 502. In the example of FIG. 5B, some of the indentations include beveled edges and slits 502-4 to accommodate a variety of gemstone cuts and sizes held in a culet down, table up fashion. As shown, any number and variety of sizes of indentations, with or without the beveled sides and slits could be included in the surface of the block 501. The example layout designs in FIGS. 5A and 5B are merely examples. Any combination of indentations may be built into the block 501 as discussed herein.

It should be noted that in FIGS. 5A and 5B, the flat portion 550 could be arranged on any side of the block surface in any kind of configuration in order to provide a visual queue to a user as to the orientation of the block. The flat portion 550 may be another shape or include features such as bumps, ridges, waves, or other visual features. The flat portion 550 may be concave, convex, or other visually identifiable shape.

Block Use Examples

Figure 6:
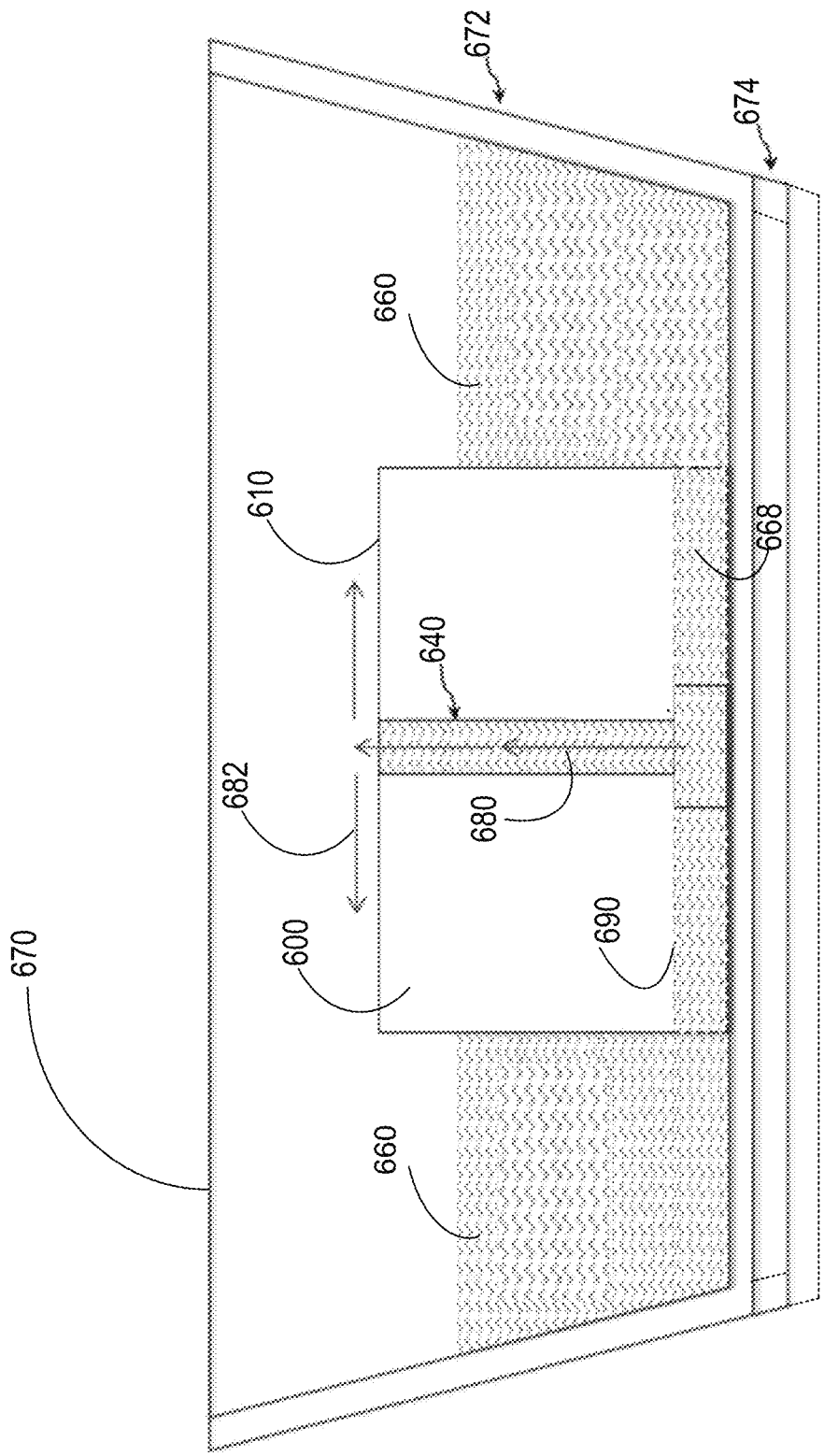
FIG. 6 is a cut away view of another example embodiment of the system described herein.

FIG. 6 shows examples of any of the variations of the cooling block in use as described herein. In the example, the block itself 600 is sitting in an open container 670. The example open container in FIG. 6 includes walls 672 and a bottom 674. In some example embodiments, the container is made of insulating material such as but not limited to Styrofoam, polystyrene, or other material with a low thermal conductivity. In some example embodiments, the bottom 674 is flat to evenly support any objects or liquid placed on it. In some example embodiments, the cooling block 600 is placed in this container 670 in use.

In some examples, when a gemstone or gemstones are being inspected, each gemstone is placed, on or in the indentations of surface 110 on block 600, and block 600 is fully or partially immersed within and in direct contact with the liquid-phase coolant in open container 670. For photoluminescence spectroscopic analysis, the diamond or gemstone may be positioned table-up. In some examples, when in use, the height of liquid nitrogen or other coolant should be less than the total height of the block and greater than the height of the arches (130 in FIG. 1A, etc.) to allow liquid nitrogen or other coolant to flow through the vertical channel (140 in FIG. 1A, etc).

In some example embodiments, the container bottom 674 is not a completely flat bottom but includes a rim which allows ambient air to be trapped between the surface the container 670 is resting on, and the bottom of the open container 670. In some example embodiments, such a rim may both support the container 670 and also allow warmer, ambient air to flow and/or sit under the container 670. Such a cooling apparatus and method may reduce or eliminates gas bubbles in 660 and help control the intensity of coolant evaporation.

As shown in the example in FIG. 6, the cooling block 600 is resting in the open container 670. In the example, a coolant such as a liquid 660 may be placed into the container 670. Such a liquid may be used to cool the block 600 and also purge the atmosphere at the liquid-air interface in container 670 around the block 600 as coolant evaporates and forms vapor. In some examples, the liquid 660 is liquid nitrogen.

When the liquid nitrogen 660 or other coolant is placed into the open container 670, it may then surround the cooling block 600 and flow in and around the bottom of the block 600. When the coolant 660 is added, the space above liquid-phase coolant may fill with the gaseous phase of coolant 660. As such, any kind of probe (not pictured) used in analysis may be positioned within this gaseous phase during the inspecting process.

Such a cooling apparatus and method may reduce ambient humidity and atmosphere at liquid-air interface. As a result, light may pass in and around the samples and block 600 without interruption while keeping humidity down. Thereby, an object can be tested for a much longer time without concern that coolant will quickly evaporate and object will become frosted.

In example embodiments in which the block is made out of thermally conductive material, the block 600 will cool to nearly, or to the same temperature of the liquid nitrogen 660. Thus, anything that comes in contact with the block 600 will also be rapidly cooled, such as a gemstone which may be placed into the indentations on the surface 610 of the block 600 as described herein.

As described in FIG. 2B and FIG. 3A, the bottom of the block 690 may include both legs 228 and arches 230 (from FIG. 2B) that together with the raised bottom 690, form a chamber 668 inside and under the block 600 when sitting in a normal upright position, as shown in FIG. 6. The block 600 also includes a central hole or chamber 640 which runs from the surface 610 to the bottom 690 of the block. In use, due to the temperature differences in the liquid nitrogen 660 and ambient air and block temperatures, the liquid nitrogen may boil and vaporize when it comes in contact with the air and block. This may produce an enveloping cloud of nitrogen gas.

In some example embodiments, the air trapped under the container 670 by way of the bottom rim 674 may aid in the boiling process by placing warmer air under the container 670 floor. When the nitrogen boils 600, nitrogen gas may bubble up 680 through the central hole 640 and spill out 682 onto the surface 610 of the block 600, thus enveloping the block from the top. In the example embodiments where the indentations are formed on the surface of the block 610, a layer of liquid nitrogen and/or vaporized nitrogen may flow over 682 the indentations and/or gemstones placed in the indentations. In so doing, the layer of cooled nitrogen 682 may cool the gemstones as well as surround the gemstones in nitrogen gas. In some embodiments, this may help remove moisture from the gemstones and thereby avoid interference from ice crystals because the liquid nitrogen film insulates the gemstones from moist in the ambient air.

In some examples, the open container 670 may be made of Styrofoam or other similar insulating material with low thermal conductivity. In some examples, the open container is made of fiberglass, polyurethane, polystyrene, glass, and/or plastic.

It should be noted that any kind of sample could be cooled and analyzed in a similar fashion. The use of gemstones as the objects being cooled and analyzed is merely an example and not intended to be limiting. Biological samples may be cooled and analyzed in a similar way. In such examples, the indentations on the block may be altered or adjusted to accommodate whatever material or object is under inspection or to be cooled.

More Alternative or Additional Block Embodiment Features

Figure 7A:
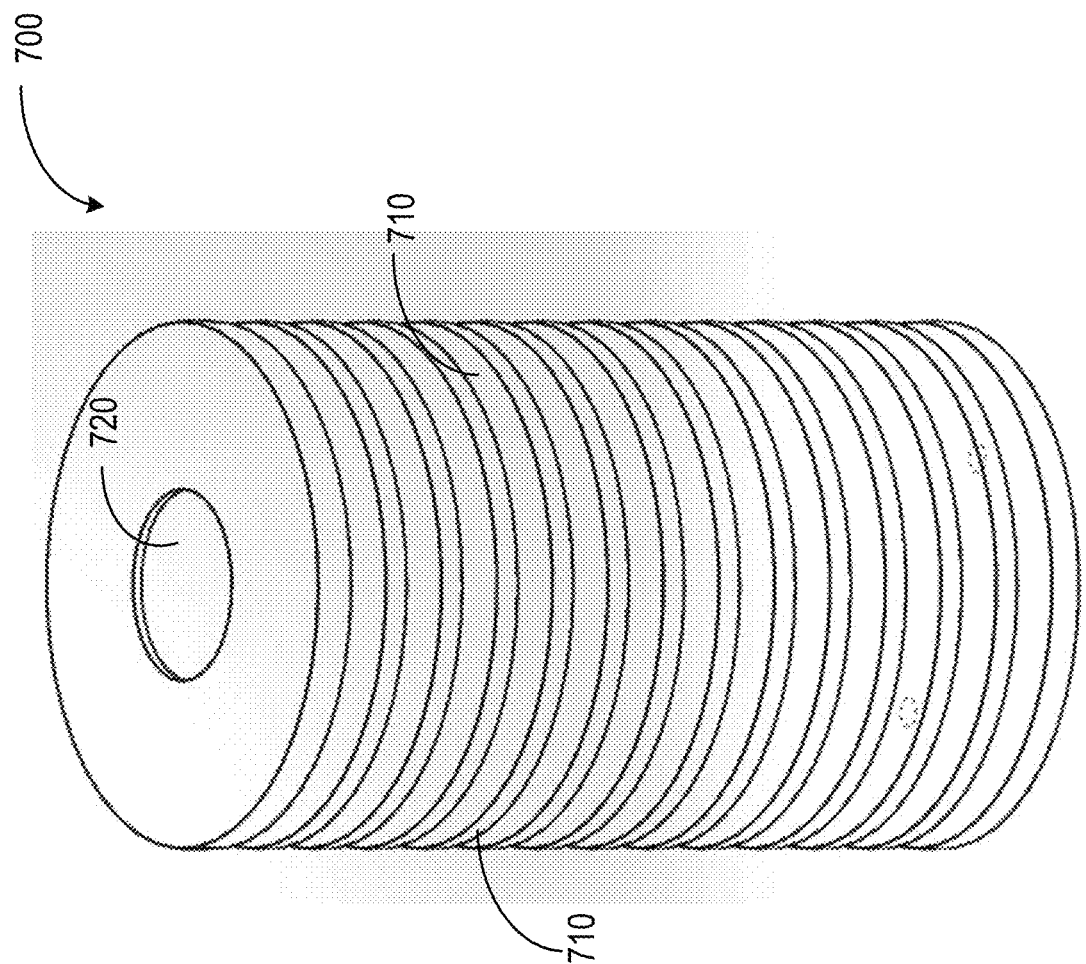
FIG. 7A is a perspective view of an embodiment of the system described herein.
Figure 7B:
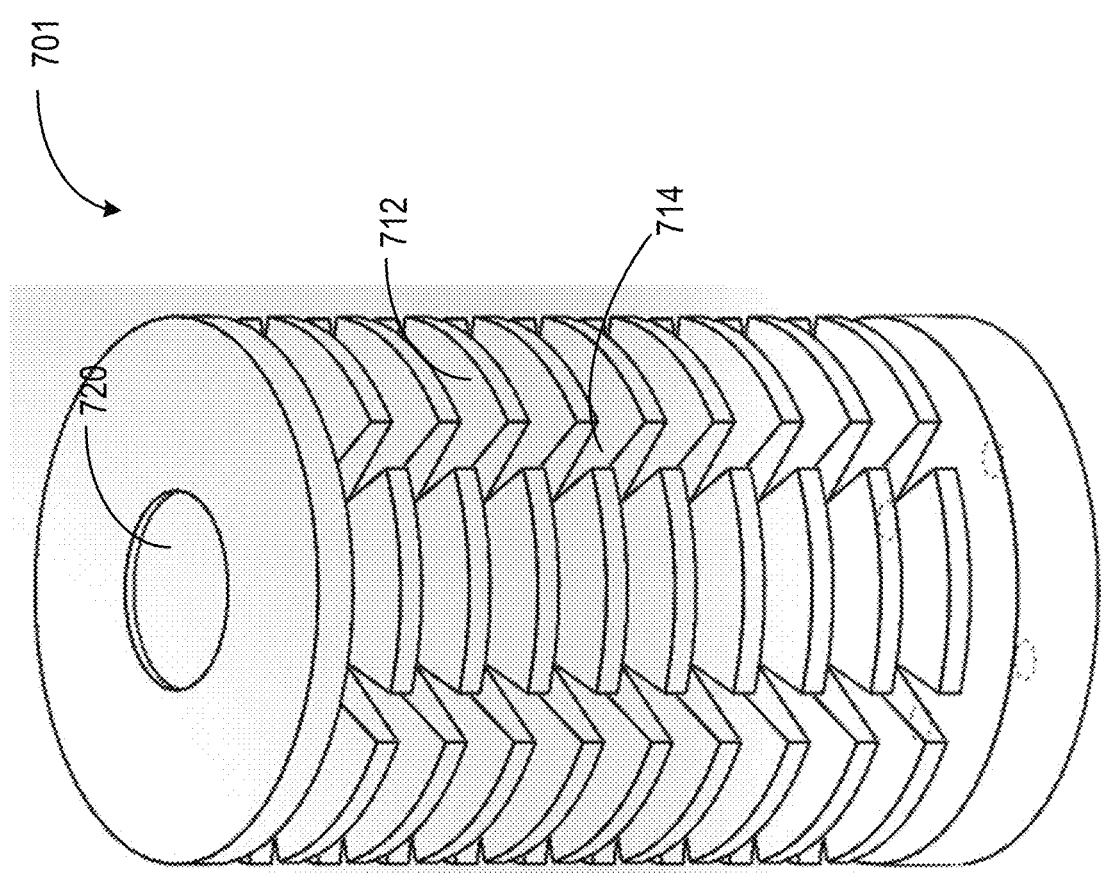
FIG. 7B is another perspective view of an embodiment of the system described herein.
Figure 7C:
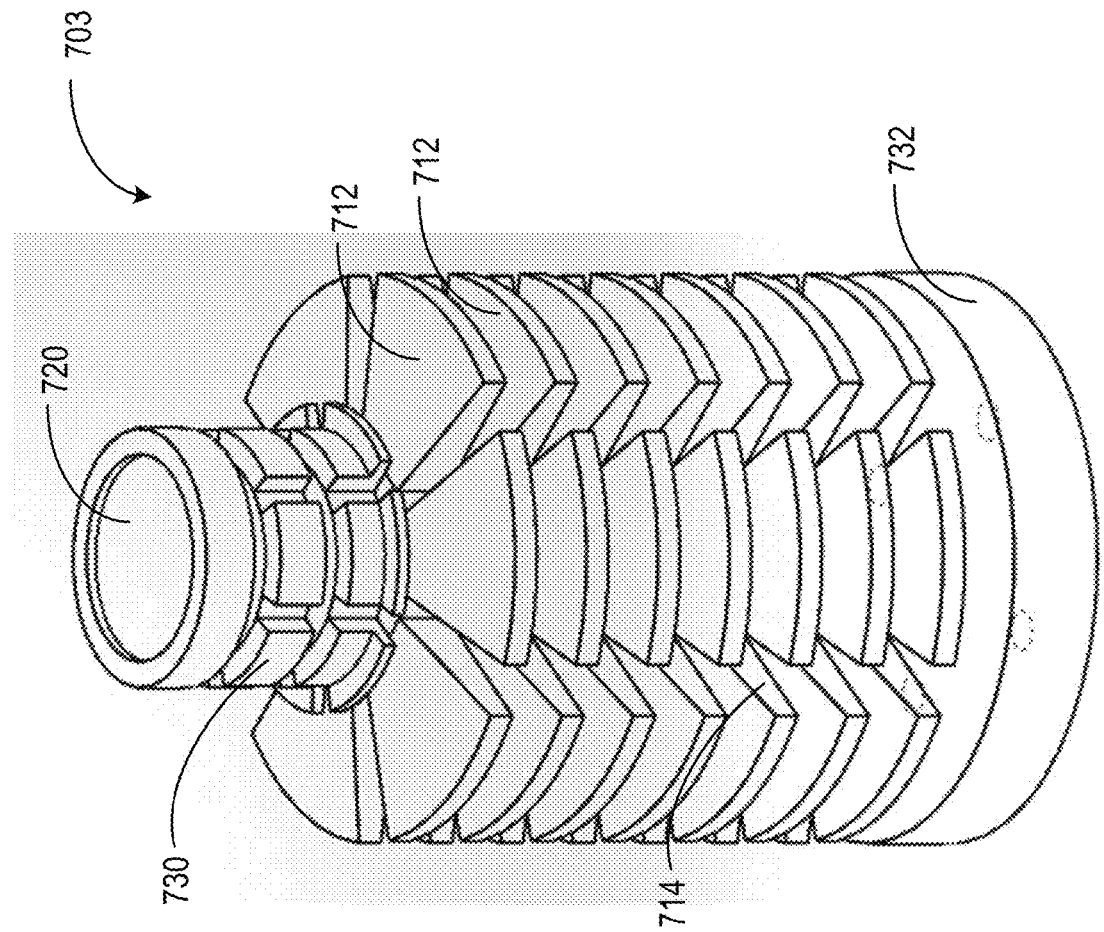
FIG. 7C is another perspective view of an embodiment of the system described herein.

FIGS. 7A, 7B and 7C show perspective views of different cooling block embodiments for a single stone, including embodiments with layered fins. In such examples, the layered fins provide more surface area for the block which is able to cool quicker than if the block did not have such fins. Such fins might also allow the liquid/gaseous nitrogen to reach the stones faster.

The example of FIG. 7A shows the block arranged with layers of fins 710. These fins 710 are shown as rings encircling the central portion 720. In this embodiment of FIG. 7A, the block is similar to those in previous embodiments, with the addition of layered rings 710 adding surface area to the block.

FIG. 7B shows another embodiment of the block 701, where the ring shaped fins 712 include or are separated by notches 714 or cutouts in each layer. These example notches 714 are shown as V shaped cutouts on each layered ring 712 to add surface area to the block. In such examples, the layered rings 712 are cut or formed with portions missing, to form the notches 714. These notched formations could be created by removing or grinding the layered rings 712 out of one block of material, or could be made by assembly, and attaching each layered ring 712 to a central core 720. In such examples, the layered rings 712 could be held in place by any number of ways including but not limited to a tongue and groove, a wedge, a screw portion, a snap portion, or other way. The V shaped cutouts 714 are shown only as an example, and the notches 714 could be any shape for example trapezoidal, rectangular, circular, slits, or other shape. The example shown in FIG. 7B where all the notches line up, is not intended to be limiting. In some examples, the notches 714 could be alternating for each layer 712. In some examples, the layers and notches could be offset, creating a spiraling set of notches around the block 701.

FIG. 7C shows another design block 703 with different features which could be employed alternatively or additionally. In the example of FIG. 7C show the fins 712 and cutout notches 714 but also shallow fins or nodes 730, in this example, at the top of the block 703. These nodes 730 in this example are protrusions that stick out from the main block 703 core and thereby increase the surface area of the overall system. The example shows these nodes as rectangular in shape but various examples could have rounded nodes, triangularly shaped nodes, waves, hexagonal nodes, or any other shape that protrudes from the block 703 to add surface area. The figure depicting a rectangular shape is not intended to be limiting. In the example, a main base 732 holds up and supports the tower of fins 712 and shallow fins 730 and the top gem support structure 720.

FIG. 8A shows a perspective drawing of the block system 801 as shown in FIG. 1A, etc. with central channel 840, top table 810, base channel 830, indentations 802, flat face portion 850, but also additional, optional, features such as fins 812 and grooves 816 that add surface area to the block 801, more similar to the designs of FIG. 7A-C. In such examples as FIG. 8A, the additional features of fins 812 could be any number in size and be of any thickness. In the example, the same piece of material includes removed grooves 816 cut into the block 801 to form the fins 812 at regular intervals up the side of the block 801 sides. These concentric ring grooves 816 forming the concentric ring fins 812 may be any depth, including but not limited to 1-5 mm, 5-10 mm, 10-50 mm, or any intermediary depth. In some example embodiments, the fins 812 and grooves 816 could be of different widths in different portions of the block 801 and may not be uniformly spaced or shaped, as shown in FIG. 8A. In some examples, as in FIG. 8A, the grooves 816 and fins 812 may be uniformly shaped and spaced.

FIG. 8B shows a back side perspective of the same embodiment shown in FIG. 8A. It should be known that the fin 812 and groove 816 features could be integrated with any of the other examples described herein, including the variously shaped indentations, slits and channels, or other features in any combination or permutation.

FIG. 8C shows an example cutaway view of the same example block 801 as shown in FIG. 8A. In the cutaway view, the main central channel 840 is shown with the top including thread or screw features for mating with a handle/screw eye. The fins 812 are shown as concentric rings around the body of the block 801 interspersed by concentric ring grooves 816. The main channel 840-2 is shown connecting the top table 810 and bottom surface 890 with the feet 828 and arches 830 as in the other example embodiments in FIGS. 1A-B etc.

As can be seen in FIG. 8C, the example shows that each of the fins 812 has a slight chamfered edge and the grooves 816 are not cut at 90 degree angles to the block 801. In some examples, the fins could be cut at 90 degree angles, but in the example in FIG. 8C, the fins 812 have thicker portions toward the inside of the block 801 than the outside. This example, alternatively or additionally, has a groove 816 that is thinner toward the inside of the block 801 and slightly wider at the outside of the block 801.

FIG. 8D shows a side view of the example of FIG. 8A-C but not as a cut away as in FIG. 8C. FIG. 8D shows the fins 812 and the bottom arches 830 as well as the other optional features such as the grooves 816. As can be seen in the example of FIG. 8D, the fins are slightly thicker toward the inside of the block 801 than the outside, thus the chamfered edge surface 818 of each fin 812 can be seen in the figure. As described, these chamfered edges are optional and could be implemented in an embodiment or not.

CONCLUSION

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more targets, that word covers all of the following interpretations of the word: any of the targets in the list, all of the targets in the list and any combination of the targets in the list.

Although certain presently preferred implementations of the invention have been specifically described herein, it will be apparent to those skilled in the art to which the invention pertains that variations and modifications of the various implementations shown and described herein may be made without departing from the spirit and scope of the invention. Accordingly, it is intended that the invention be limited only to the extent required by the applicable rules of law.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

Although some presently preferred implementations of the embodiments have been specifically described herein, it will be apparent to those skilled in the art to which the embodiments pertain that variations and modifications of the various implementations shown and described herein may be made without departing from the spirit and scope of the embodiments. Accordingly, it is intended that the embodiments be limited only to the extent required by the applicable rules of law.

We claim:

1. A cooling stage, comprising:
    a main homogenous solid body formed of a non-insulating thermo-conductive metal material, the main homogenous solid body including,
        a top surface including a plurality of indentations, wherein the plurality of indentations each have side walls and a flat bottom formed from the main homogenous solid body of non-insulating thermo-conductive metal material, wherein a depth of the plurality of indentations from the top surface is between 0.1 mm and 0.7 mm,
        wherein the plurality of indentations include at least three groupings,
            a first grouping of indentations that have a smaller diameter than a second grouping of indentations,
            the second grouping of indentations having a larger diameter than the first grouping of indentations, and
            a third grouping of indentations, wherein each indentation of the third grouping of indentations comprises at least two slit indentations radiating from a respective indentation of the third grouping, wherein each slit extends beyond the circumference of the respective indentation of the third grouping;
        a bottom surface of the main homogenous solid body made of non-insulating thermo-conductive metal material having a plurality of leg structures along the edge of the bottom surface, each leg formed from the main homogenous solid body of non-insulating thermo-conductive metal material, wherein between each leg structure is an arch, and wherein the bottom surface and the plurality of leg structures form a partially enclosed bottom chamber; and
        a channel through a center region of the main homogenous solid body, connecting the top surface and the bottom chamber.

2. The cooling stage of claim 1, wherein the non-insulating thermoconductive metal material comprises aluminum, gold, silver, copper, bronze, molybdenum, tungsten, beryllium oxide, aluminum nitride, brass, iron, steel, nickel, carbon steel, lead, gallium nitride, zinc, tin, a tungsten carbide, graphite, cadmium, magnesium, monel, palladium, platinum, rhodium, tantalum, thallium, thorium, titanium, vanadium, a zinc alloy, a copper alloy, an aluminum alloy, a magnesium alloy, a nickel alloy, a beryllium alloy, and combinations thereof.

3. The cooling stage of claim 1, wherein the plurality of indentations comprises compartments of different sizes.

4. The cooling stage of claim 1, wherein the main body has a top dimension and a bottom dimension that are the same.

5. The cooling stage of claim 1, wherein a horizontal cross section of the main body has a shape selected from the group consisting of a circle, an oval, a polygon with 3 or more sides, a triangle, a square, a rectangle, a diamond, a pentagon, a hexagon, a heptagon, an octagon, and an irregular shape.

6. The cooling stage of claim 1, wherein each of the plurality of leg structures has a horizontal dimension that is larger than that of the arch between two leg structures.

7. The cooling stage of claim 1, wherein the plurality of leg structures comprises two to six leg structures.

8. The cooling stage of claim 1, further comprising:
    a handle capable of securely engaging with the main body of the cooling stage.

9. The cooling stage of claim 8, wherein the handle is configured to engage with the channel by screw threads on the channel and matching screw threads on the handle.

10. The cooling stage of 1, wherein the channel has a horizontal dimension that is between 5% and 10% of the horizontal dimension of the main body.

11. The cooling stage of claim 1, wherein a horizontal cross-section of the channel has a shape selected from the group consisting of a circle, an oval, a polygon with 3 or more sides, a triangle, a square, a rectangle, a diamond, a pentagon, a hexagon, a heptagon, an octagon, and an irregular shape.

12. The cooling stage of claim 1, wherein the bottom chamber has a height that is between 5% to 10% of the height of the main body.

13. A cooling system, comprising:
    a cooling stage, wherein the cooling stage comprises:
        a main homogenous solid body formed of a thermo-conductive material, the main homogenous solid body further comprising:
            a top surface including a plurality of indented compartments, wherein the plurality of indented compartments on the top surface each include sidewalls and a bottom formed from the main homogeneous solid body, wherein a depth of the plurality of indented compartments from the top surface is between 0.1 mm and 0.7 mm, wherein the plurality of indented compartments include indentations with at least two different diameters, wherein at least some indentations include at least two slit indentations radiating from a respective indentation beyond the circumference of the respective indentation;

a bottom surface having a plurality of leg structures along the edge of the bottom surface, wherein each leg structure is flanked by a space on either side, and wherein the bottom surface and the plurality of leg structures form a partially enclosed bottom chamber; and a channel through a center region of the main homogenous solid body, connecting the top surface and the bottom chamber; a container in which the cooling stage is placed, the container having a continuous lip around its bottom edge, the lip forming a recessed bottom; and a coolant inside the container, the coolant surrounding the cooling stage.

14. The cooling system of claim 13, wherein the container has a flat inner bottom surface in contact with each leg structure.

15. The cooling system of claim 13, wherein the container is made of a thermo-insulating material.

16. The cooling system of claim 13, wherein the coolant is liquid nitrogen.

17. The cooling system of claim 13, wherein the thermo-conductive material is selected from the group consisting of a metal, a carbon-based material, a ceramic material, a thermal conductive composite, a thermal conductive polymer, an alloy, a silicate-based material, and combinations thereof.

18. The cooling system of claim 13, wherein the thermo-conductive material comprises aluminum, gold, silver, copper, bronze, molybdenum, tungsten, beryllium oxide, aluminum nitride, silicon carbide, brass, iron, steel, nickel, carbon steel, lead, gallium nitride, zinc, tin, a tungsten carbide, graphite, cadmium, germanium, magnesium, monel, palladium, platinum, rhodium, tantalum, thallium, thorium, titanium, vanadium, a zinc alloy, a copper alloy, an aluminum alloy, a magnesium alloy, a nickel alloy, a beryllium alloy, and combinations thereof.

19. The cooling system of claim 13, wherein at least one indentation has a flat bottom for receiving a sample.

20. The cooling system of claim 13, wherein a horizontal cross section of the main homogenous solid body has a shape selected from the group consisting of a circle, an oval, a polygon with 3 or more sides, a triangle, a square, a rectangle, a diamond, a pentagon, a hexagon, a heptagon, an octagon, and an irregular shape.

21. The cooling system of claim 13, wherein each of the plurality of leg structures has a horizontal dimension that is larger than that of a space between two leg structures.

22. The cooling system of claim 13, wherein the plurality of leg structures comprises two to six leg structures.

23. The cooling system of claim 13, wherein the height of the lip along the bottom edge of the container is adjustable.

* * * * *